United States Patent [19]

Cullen et al.

[11] Patent Number: 4,908,316

[45] Date of Patent: Mar. 13, 1990

[54] STREPTOMYCES SP. N664-30 WHICH PRODUCES AN IONOPHORE ANTIBACTERIAL AGENT

[75] Inventors: Walter P. Cullen, East Lyme; John R. Oscarson, Gales Ferry, both of Conn.; Junsuke Tone; Hiroshi Maeda, both of Chita, Japan

[73] Assignee: Pfizer Inc., New York, N.Y.

[21] Appl. No.: 161,630

[22] Filed: Feb. 29, 1988

Related U.S. Application Data

[62] Division of Ser. No. 902,353, Aug. 29, 1986.

[51] Int. Cl.$^4$ .......................... C12N 1/20; C12P 1/06; C12R 1/465
[52] U.S. Cl. ................................ 435/253.4; 435/169; 435/886
[58] Field of Search ...................... 435/253.4, 169, 886

[56] References Cited

PUBLICATIONS

LIV, C. et al., *J. Antibiotics*, vol. 36(9) pp. 1118–1122, Sep., 1983.
LIV, C. et al., *J. Antibiotics*, vol. 34(10) pp. 1241–1247, Oct., 1981.
LIV, C. et al., *J. Antibiotics*, vol. 29(1) pp. 21–28, Jan., 1976.

*Primary Examiner*—Jayme A. Huleatt
*Attorney, Agent, or Firm*—Peter C. Richardson; J. Trevor Lumb; James M. McManus

[57] ABSTRACT

An antibiotic has been isolated from fermentation of a new Streptomyces culture. The new ionophore is active as an antibacterial and anticoccidial agent.

1 Claim, No Drawings

STREPTOMYCES SP. N664-30 WHICH PRODUCES AN IONOPHORE ANTIBACTERIAL AGENT

CROSS REFERENCE TO RELATED APPLICATIONS

This application is a divisional application of co-pending application 902,353, filed Aug. 29, 1986.

BACKGROUND OF THE INVENTION

This invention relates to a new antibiotic which is derived from fermentation of a new Streptomyces culture, designated N664-30, obtained from a soil sample from the United Kingdom. In addition to antibacterial activity, the compound of the instant invention is also useful as an anticoccidial agent.

Structurally the new antibiotic of this invention is a new member of the acidic polycyclic ether (ionophore) antibiotics. This family of antibiotics includes dianemycin [J. Antibiotics, 22, 161 (1969)]and ibid., 33, 137 (1980); monensin [J. Amer. Chem. Soc., 89, 5737 (1967)]; salinomycin [J. Antibiotics, 27, 814 (1974)]; Antibiotic TM-531 disclosed in U.S. Patent No. 4,269,971 and Antibiotic 53,607 disclosed in U.S. Patent No. 4,361,649.

SUMMARY OF THE INVENTION

This invention provides a new ionophore antibacterialanticoccidial agent of the following structure:

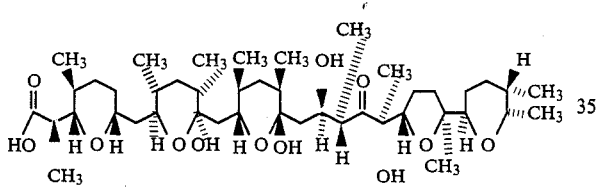

Since the structure of this ionophore is tentative (98% confidence), the invention comprises a compound having the physical and chemical properties described herein.

This invention also comprises a biologically pure culture of the microorganism Streptomyces sp. N664-30 and the use of the compound of the present invention as an antibacterial and anticoccidial agent.

DETAILED DESCRIPTION OF THE INVENTION

The antibiotic ionophore of the present invention is produced by fermentation of a new microorganism designated as culture N664-30, which was obtained from a soil sample collected in England. Culture N664-30 was characterized and identified by Liang H. Huang, Ph.D., Pfizer Inc., Groton, Conn., USA, as described hereinbelow.

On examination, culture N664-30 possessed narrow hyphae of the actinomycetes, grey aerial mycelium with coiled spore chains and unfragmented substrate mycelium, features characteristic of members of Streptomyces.

The slant culture N664-30 was planted into ATCC 172 broth and grown for four days at 28° C. on a shaker. It was then centrifuged for 20 minutes, washed three times with sterile distilled water and planted on media commonly used for identification of members of the Actinomycetales.

The culture was incubated at 28° C. and the results might be read at varying times but most commonly were taken at 14 days. The colors were described in common terminology, but exact colors were determined by comparisons with color chips from the Color Harmony Manual, fourth edition. The methods of whole-cell amino acid and sugar analyses are those described in Becker, B. et al., Appl. Microbiol. 12:421-423, 1964; and in Stanech, J. L., et al., Appl. Microbiol., 28, 226–231 (1974). For the comparison purpose, the type strain of Streptomyces libani ATCC 23732 was used.

Identification media used for the characterization of the culture and references for their composition are as follows:

1. Tryptone Yeast Extract Broth-(ISP #1 medium, Difco).
2. Yeast Extract-Malt Extract Agar-(ISP #2 medium, Difco).
3. Oatmeal Agar-(ISP #3 medium, Difco).
4. Inorganic Salts-Starch Agar-(ISP #4 medium, Difco).
5. Glycerol-Asparagine Agar-(ISP #5 medium, Difco).
6. Peptone-Yeast Extract Iron Agar-(ISP #6 medium, Difco).
7. Czapek-Sucrose Agar-S. A. Waksman, The Actinomycetes, Vol. 2, medium No. 1, p. 328, 1961.
8. Glucose-Asparagine Agar-Ibid, medium No. 2, p. 328.
9. Bennett's Agar-Ibid, medium No. 30, p. 331.
10. Emerson's Agar-Ibid, medium No. 28, p. 331.
11. Nutrient Agar-Ibid, medium No. 14, p. 330.
12. Gordon and Smith's Tyrosine Agar-R. E. Gordon and M. M. Smith, J. Bacteriol. 69:147-150, 1955.
13. Casein Agar-Ibid.
14. Calcium Malate Agar-S. A. Waksman, Bacteriol. Rev. 21:1-29, 1957.
15. Gelatin-R. E. Gordon and J. M. Mihm, J. Bacteriol. 73:15-27, 1957.
16. Starch-Ibid.
17. Organic Nitrate Broth-Ibid.
18. Dextrose Nitrate Broth-S. A. Waksman, The Actinomycetes, Vol. 2, medium No. 1, p. 328, 3 g dextrose substituted for 30g sucrose and agar omitted.
19. Potato Carrot Agar-M. P. Lechevalier, J. Lab. and Clin. Med. 71:934–944, 1968, but use only 30 g potatoes, 2.5 g carrots and 20 g agar.
20. 2% Tap Water Agar.
21. Skim Milk-Difco.
22. Cellulose utilization—
   (a) H. L. Jensen, Proc. Linn. Soc. N.S.W. 55:231-248, 1930.
   (b) M. Levine and H. W. Schoenlein, A Compilation of Culture Media, medium No. 2511, 1930.
23. Carbohydrates-ISP #9 medium, Difco.
24. Temperature Range-ATCC medium 196 in ATCC Media Handbook, 1st ed., p. 11, 1984.

Yeast Extract-Malt Extract Agar—Growth moderate to good; white, pale gray to yellowish-gray brown (near gray series 2 cb, 2 dc, 2 gc, 4 ie); moderately raised, wrinkled, aerial mycelium white to pale gray; reverse yellowish gray to brown (2 gc, 2 ie, 4 ie); soluble pigment none to yellowish (2 lc).

Oatmeal Agar—Growth poor to moderate; cream, off-dc); slightly raised, smooth, aerial mycelium offwhite to pale gray; reverse cream (1½ ca); soluble pigment cream (1½ ca).

Inorganic Salts-Starch Agar—Growth moderate, cream to pale gray (2 ca, near gray series 2 dc), slightly to moderately raised, smooth but wrinkled near end of streak, aerial mycelium pale gray; reverse pale yellowish to brown (2 ea, 3 lg); no soluble pigment.

Glycerol-Asparagine Agar—Growth moderate to good, whitish gray to pale gray (near gray series 2 dc), moderately raised, granular to wrinkled, aerial mycelium same as surface; reverse pinkish gray (3 ge, 3 ig); soluble pigment pale yellowish (2 ea).

Czapek-Sucrose Agar—Growth poor to moderate, pale gray (near gray series 2 cb), thin, smooth, aerial mycelium pale gray; reverse colorless to cream (1½ ca); no soluble pigment.

Glucose-Asparagine Agar—Growth moderate to good, whitish gray to pale gray (near gray series 2 cb, 2 dc), moderately raised; smooth, granular to slightly wrinkled; aerial mycelium same as surface; reverse pale yellowish to pinkish gray (2 ea, 3 ge, 3 ig); soluble pigment yellowish (2 ga).

Gordon and Smith's Tyrosine Agar—Growth moderate, cream (2 ca), slightly raised, smooth, no aerial mycelium; reverse cream (2 ca); soluble pigment pale yellowish (2 ea).

Calcium Malate Agar—Growth poor, colorless to white (near gray series 2 ba), thin, smooth; with sparse white, aerial mycelium; reverse colorless; no soluble pigment.

Casein Agar—Growth moderate; white, pale gray, tan to brown (near gray series 2 cb, 3 gc, 3 ie); slightly raised, smooth, aerial mycelium white to pale gray; reverse yellowish to tan (2 ga, 3 gc); soluble pigment tan (3 gc).

Bennett's Agar—Growth good, pale gray (near gray series 2 dc), moderately raised, wrinkled, aerial mycelium pale gray; reverse grayish yellow to gray (2 le, near gray series 2 ih); soluble pigment pale yellowish (2 ea).

Emerson's Agar—Growth good; white, pale gray to tan (near gray series 2 cb, 3 gc), moderately raised, wrinkled, aerial mycelium white to pale gray; reverse tan (3 gc); no soluble pigment.

Nutrient Agar—Growth poor to moderate, cream (2 ca), thin, smooth, no aerial mycelium; reverse cream (2 ca); no soluble pigment.

Gelatin Agar—Growth moderate, cream (2 ca), slightly raised, smooth, no aerial mycelium; reverse cream (2 15 ca); no soluble pigment.

Starch Agar—Growth moderate to good, white to cream (2 ca), moderately raised, smooth to slightly wrinkled, aerial mycelium white; reverse cream (2 ca); no soluble pigment.

Potato Carrot Agar—Growth poor to moderate, pale gray (near gray series 2 cb), thin to slightly raised, smooth, aerial mycelium pale gray; reverse colorless to cream (1 ba); no soluble pigment.

Tap Water Agar—Growth poor, colorless to white (near gray series 2 ba), thin, smooth; with sparse, white aerial mycelium; reverse colorless; no soluble pigment.

Morphological Properties—The morphological properties were observed on glucose-asparagine agar after 15 days of incubation: spore mass in Gray-color series; Spore chains in Section Spirales, coiled, moderately open, of small diameter, 2 to 9 turns per spore chain, sometimes being irregularly or compactly coiled, or flexuous; 10 to 50 spores per spore chain; sporophores monopodially or verticillately branched; spores globose, oval, elliptical to rod-shaped, 0.7–1.2 μm diam or 1.2–2.0×0.6–1.1 μm; smooth, as revealed by scanning electron microscopy.

Biochemical Properties—Melanin not produced; hydrogen sulfide not produced; gelatin liquefied; starch hydrolyzed; nitrate not reduced to nitrite; no growth and no decomposition on both cellulose broths; no coagulation and no peptonization on milk; casein digestion positive; calcium malate digestion negative; tyrosine digestion negative. Carbohydrate utilization: glucose, fructose, mannitol, raffinose, rhamnose, sucrose, and xylose utilized; arabinose and inositol not utilized.

| Temperature Relations- | | | |
|---|---|---|---|
| 21° C. | 28° C. | 37° C. | 45° C. |
| Good Growth | Good Growth | Moderate to Good | No Growth |

Cell Wall Analyses: The whole-cell hydrolysates contain LL-diaminopimelic acid, glucose, mannose and rhamnose.

The culture N664-30 is characterized by the gray aerial mycelium, the coiled spore chains, the negative melatin reaction and the spores with a smooth surface. The whole-cell hydrolysates contain LL-diaminopimelic acid but no diagnostic sugars. It is similar to *Streptomyces libani* in many of the biochemical properties. The culture N664-30 differs in the inability to clear milk, the inability to utilize inositol and the ability to utilize rhamnose. The aerial mycelium of *S. libani*, unlike that of culture N664-30, shows slightly darker gray tint on some media and may become black on inorganic salts-starch agar and potato carrot agar. Thus, culture N664-30 is considered as a member of the genus *Streptomyces* and designated as *Streptomyces* sp. It has been deposited at the American Type Culture Collection with the accession number 53523.

The permanency of the deposit of this culture at the American Type Culture Collection at Rockville, Md. and reayy accessibility thereto by the public are afforded throughout the effective life of the patent in the event the patent is granted. Access to the culture is available during the pendency of the application under 37 CFR 1.14 and 35 USC 112. All restrictions on the availability to the public of the culture deposited will be irrevocably removed upon granting of the patent.

The procedures used to produce the antibiotic of the present invention are familiar to those skilled in the art. The antibiotic is produced by a species of Streptomyces represented by culture N664-30. The antibiotic was isolated by extraction of the whole broth at natural pH with methylisobutyl ketone and concentration of the solvent to a viscous oil. The oil was suspended in heptane and batch treated with silica gel 60. The silica gel cake was eluted with chloroform, chloroform/ethyl acetate, ethyl acetate and ethyl acetone/acetone. After concentration, the chloroform/ethylaacetate fraction yielded a small amount of crude product from which the desired compound was crystallized as the mixed sodium/potassium salt.

The Streptomyces culture can be grown from 24° to 36° C. under submerged conditions with agitation and aeration on media consisting of carbohydrate sources such as sugars, starches, glycerol; orqanic nitrogen substances such as soybean meal, casamino acids, yeast extract; growth substance such as grain solubles, fish meal, cotton seed meal; mineral salts containing trace elements such as iron, cobalt, copper, zinc etc. and calcium carbonate or phosphates as buffering agents. The antibiotic can be recovered by extracting the whole broth with various organic solvents such as n-butanol, methylisobutyl ketone, or chloroform, to name a few, at pH ranges from 4.0 to 8.0, or separating the mycelium after growth has been completed, and extracting the mycelium; the filtrate can be discarded. The solvent is concentrated to a thin syrup, dissolved in heptane and chromatographed on silica gel to obtain the pure compound.

Inoculum is prepared by scraping vegetative cells from slants or Roux bottles inoculated with the N664-30 culture. A solid medium suitable for initial growth on slants and roux bottles is ATCC medium #172.

| ATCC 172 | Grams/liter |
|---|---|
| Glucose | 10 |
| Soluble Starch | 20 |
| Yeast Extract | 5 |
| NZ Amine A | 1 |
| Calcium Carbonate | 1 |
| Distilled Water to 1000 ml; pH to 7.0 with KOH Add Agar | 20 |

Vegetative cells from slants are used to inoculate either shake flasks or inoculum tanks; or alternatively the inoculum tanks are inoculated from shake flasks. In shake flasks growth will generally have reached its maximum in 72 to 96 hours whereas in the inoculum tanks growth will usually be at the most favorable period in 96 to 120 hours. A fermentor is inoculated with vegetative broth from the inoculum flasks or tank under completely aseptic conditions and fermented for a period of 120 to more than 200 hours. Aeration is maintained in shake flasks by agitation on a shaker or in tanks by forcing sterile air through a sparger at the rate of ½ to 2 volumes of air per volume of broth per minute. The speed of agitation (stirring) depends upon the type of agitator employed; a shake flask is usually run at 150 to 200 cycles per minute and a fermentor at 300 to 1700 revolutions per minute. Sterility must be maintained at all times. The temperature is regulated between 28° C. and 36° C. Foaming during the ferentation can be controlled with sterile antifoams such as refined soybean oil, or other suitable antifoaming agent added to the makeup or to the fermentor aseptically as needed after inoculation.

Shake flasks are prepared using one of the following media:

| IT2 | Grams/liter | JDYTT | Grams/liter |
|---|---|---|---|
| Corn Steep Liq | 5 | Cerelose | 10 |
| Cerelose | 10 | Corn Starch | 5 |
| Dextrin | 20 | Corn Steep Liquor | 5 |
| Wheat Germ | 10 | NZ Amine YTT | 5 |
| Poly Peptone | 1.0 | Cobalt Chloride | 0.002 |
| Ammonium Sulfate | 1.0 | Calcium Carbonate | 3 |
| Cobalt Chloride | 0.001 | | |
| Calcium Carbonate | 4 | | |

One hundred ml of medium is distributed into 300 ml shake flasks and sterilized at 120° C. and 15 psi for 30 minutes. After cooling, the medium is inoculated with a vegetative cell suspension from the Streptomyces slant culture N664-30 grown on ATCC 172 medium in agar. The flasks are shaken at 28° C. on a rotary shaker having a displacement of 1½ to 2½ inches and 150 to 200 cycles per minute (CPM) for three to four days. One flask is used to inoculate a five liter fermentation vessel.

The progress of antibiotic production during fermentation, and the bioactivity of the fermentation broth and recovery streams, can be monitored by biological assay of the broth employing a sensitive strain of *Staphylococcus aureus* or *Bacillus subtilis*. *S. aureus* ATCC 6538 and *B. subtilis* ATCC 6633 are suitable strains for this purpose. Standard plate assay technique is employed, in which the zone of inhibition surrounding a filter paper disc saturated with the broth is used as a measure of antibiotic potency. Also, thin-layer chromatograpy employing silica gel is a useful tool for analyzing the antibiotic produced in fermentation media and the composition of crude and purified materials extracted from the fermentation broths. The components in the broth and recovery streams can be detected by using Analtech silica gel GF plates in ethyl acetate. The developed plates are sprayed with vanillin reagent (3 g vanillin in 75 ml ethanol and 25 ml 85% phosphoric acid) and heated to 80° C. The ionophore of the present invention appears as a yellow to green spot. The developed thin layer plate can also be overlayed with agar seeded with either *S. aureus* or *B. subtilis* to which 2,3,5-triphenyl-2H-tetrazolium chloride monohydrate dye has been added and incubated at 37° C. for 16 hours to visualize the antibiotic (white against a pink background).

The antibiotic of this invention can be recovered from a fermentation broth of culture N664-30 by extraction of the whole broth using a volatile, water-immiscible organic solvent such as ethyl acetate, n-butanol, chloroform or methylisobutyl ketone, at a natural pH. Alternatively, the mycelium can be removed from whole broth, and then the filtrate is extracted in the same manner as for whole broth. This affords a solution of the antibiotic complex in an organic solvent. The organic solvent is removed by evaporation in vacuo and the residue is stirred with hexane. The hexane is removed, leaving the antibiotic complex, usually as a solid. The crude antibiotic complex can be further purified by chromatography or counter-current distribution.

Base salts of the ionophore of the present invention can be prepared by conventional means known to those skilled in the art. For example, a suspension of the antibiotic in water can be treated with an equivalent of a base and the resulting solution concentrated to dryness. Base salts not only include pharmaceutically acceptable alkali and alkaline earth metal salts but also salts formed by the compound of the present invention and pharmaceutically acceptable organic bases.

The antibiotic of this invention shows antibacterial activity against certain gram-positive and gram-negative microorganisms. This antibacterial activity can be demonstrated by measuring the minimum inhibitory concentration (MIC) of the complex against a variety of organisms, according to standard procedures. Thus, the MIC's can be measured by the procedure recommended by the International Collaborative Study on Antibiotic Sensitivity Testing (Ericcson and Sherris, *Acta. Patholoqica et Microbiologia* Scandinav, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 50 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

The antibacterial activity of the antibiotic of the present invention makes it suitable for the treatment of bacterial infections caused by susceptible organisms in mammalian subjects. In particular the antibiotic substance of this invention for a salt thereof is useful in treating bacterial infections in large farm animals, e.g., horses, cows and swine, and also domestic pets, e.g., cats and dogs.

When using an antibacterial compound of this invention, or a salt thereof, in a mammal, the compound can be administered alone, or it can be mixed with other antibiotic substances and/or pharmaceutically-acceptable carriers or diluents. Said carrier or diluent is chosen on the basis of the intended mode of administration. For example, when considering an oral mode of administration, an antibacterial compound of this invention can be used in the form of syrups, elixirs, aqueous solutions and suspensions, and the like, in accordance with standard pharmaceutical practice. The proportional ratio of active ingredient to carrier will naturally depend on the dosage contemplated; however, said proportional ratio will normally be in the range from 1:6 to 6:1 by weight, and preferably 1:1 to 1:4. The antibacterial compound of this invention compound of this invention can also be administered parenterally which includes intramuscular, intraperitoneal, subcutaneous and intravenous administration. For these purposes, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compound of this invention is of use in pets and farm animals and the daily dosages to be used will not differ significantly from other macrolide antibiotics, such as tylosin. The prescribing veterinarian will ultimately determine the appropriate dose for a given subject, and this can be expected to vary according to the weight and response of the individual animal as well as the nature and severity of the animal's symptoms. The compounds of this invention will normally be used orally at dosages in the range from 20 to about 50 mg per kilogram of body weight per day, and parenterally at dosages from about 10 to 30 mg per kilogram of body weight per day, usually in divided doses. In some instances it may be necessary to use doses outside these ranges.

In addition to its use as an antibacterial agent the compound of the present invention and its base slts exhibit excellent activity against coccidiosis infection in poultry. When incorporated in the diet of chickens at a level to 50 to 200 ppm, the compound of the present invention is effective in controlling single infections of *Eimeria tenella, E. acervulina, E. maxima*, etc. and mixed infections of these organism.

Because of its end use for the prevention and treatment of coccidiosis in poultry, whole fermentation broth containing the compound of the instant invention may be taken to dryness (preferably by spray-drying) and incorporated in poultry feed at the desired antibiotic potency level.

The following examples are provided solely for further illustration.

EXAMPLE 1

To a five liter fermentation vessel containing three liters of one of the following media:

| IT-2 | grams/liter | CN-2 | grams/liter |
|---|---|---|---|
| Poly Peptone | 1.0 | Cerelose | 10 |
| Cerelose | 10.0 | Corn Starch | 10 |
| Dextrin | 20.0 | Soybean Flour | 10 |
| Corn Steep Liquor | 5.0 | NZ Amine YTT | 10 |
| Wheat Germ | 10.0 | Cobalt Chloride | 0.002 |
| Ammonium Sulfate | 1.0 | Calcium Carbonate | 1 |
| Calcium Carbonate | 4.0 | | |
| Cobalt Chloride | 0.001 | | |
| Water to 1 liter | | | |
| pH 6.9–7.0 | | | |

| JDYTT | grams/liter | | UK 1-2 | grams/liter |
|---|---|---|---|---|
| Cerelose | 10 | | Cerelose | 45 |
| Corn Starch | 5 | | Soy Flour | 10 |
| Corn Steep Liquor | 5 | or | Corn Steep Liquor | 15 |
| Cobalt Chloride | 0.002 | | Magnesium Sulfate | 0.1 |
| NZ Amine YTT | 5 | | Manganese Sulfate | 0.1 |
| Calcium Carbonate | 3 | | Cobalt Chloride | 0.002 |
| | | | Calcium Carbonate | 3.0 | was added one milliliter of L61 silicone as an antifoaming agent, then the vessel was sealed and sterilized at 120° C. and 15 psi for 45 minutes. Each fermentation was inoculated with the contents of one shaker flask and fermented for 120 to 168 hours at 32° C., stirred at 1700 revolutions per minute with an air rate of one volume of air per volume of liquid per minute.

When the fermentation was completed (based on an antibiotic disc assay versus *B. subtilis* ATCC 6633) the fermentors were stopped, filtered at the natural pH with the aid of a filter aide such as Hyflo ® Super-Cel or Celite. The filter cake was slurried in methanol, concentrated in vacuo, diluted with 2–3 volumes of water then extracted 2X with ⅓ to ¼ volume of a solvent such as methylisobutyl ketone or n-butanol. The solvent layer was separated from the aqueous phase by aspiration or centrifugation, sparkled, and concentrated in vacuo to a viscous oil.

The bioactivity of the broth, and subsequent recovery streams can be followed by using a sensitive strain of *Bacillus subtilis* ATCC 6633 or *Staphylococcus aureus* ATCC 6538. The components in the broth and recovery streams can be visualized by using Analtech silica gel GF plates in the following system: neat ethyl acetate. The developed plates are sprayed with vanillin reagent (3 g vanillin in 75 ml ethanol and 25 ml 85% .phos-phoric acid) and heated to 80° C. The ionophore appears as a yellow to green spot. The developed tlc plate can also be overlayed with agar seeded with either *S. aureus* or *B. subtilis* to which tetrazolium dye has been added and incubated at 37° C. for 16 hours to visualize the antibiotic (white against a pink background).

EXAMPLE 2

Scale-up in large fermentors was carried out by preparing shake flasks containing 0.7 liters of UK 1–2 or JDYTT medium. The shake flask inoculum was fermented for 4 to 6 days at 28° C., and used to inoculate a 50 or 1700 gallon fermentor containing 25 gallons of UK 1-2 medium or 1200 gallons of JDYTT medium. Approximately one liter of inoculum was used in the tanks. The fermentor, after fermenting 5 to 7 days, was harvested (ca. 25 or 1100 gallons). The whole broth was extracted with ⅓ volume of methylisobutyl ketone at natural pH, separated on an alpha Delaval separator or a Podbielnack extractor and the solvent concentrated in vacuo to an oil.

The oil was further concentrated on a cyclone evaporator to a syrup. After conentration, the oil was suspended in heptane, stirred with silica gel (Woelm silica gel 60), then filtered through a bed of silica gel and washed repeatedly with heptane. The antibiotic was eluted stepwise with chloroform, chloroform/ethyl acetate, ethyl acetate and finally 50% acetone in ethyl acetate. The elution was followed by thin layer chromatography and bioassay of the fractions. The active cuts (chloroform/ethylacetate) were combined, concentrated and rechromatographed to isolate the desired antibiotic. The yield from the small fermentor, ca 25 gals, was 2.8 g.

EXAMPLE 3

The whole broth of a small tank fermentation of culture N664-30 (total volume approximately 100 liters) was extracted with one third volume of methylisobutyl ketone. The extract was concentrated under vacuum to a brownish oil (30 g).

This oil was chromatographed on a 5×100 cm column packed with column grade silica gel (Woelm, 70-230 mesh) in chloroform. The column was eluted with chloroform at 10 ml/min and fractions of 10 ml each were collected. After the first color appeared in the collected fractions the elution solvent was changed to ethyl acetate - chloroform (2:1).

These fractions were examined by thin-layer chromatography on Analtech silica gel GF plates developed in ethyl acetate. The plates were sprayed with a solution of 3% vanillin in ethanol - 85% phosphoric acid (3:1) and then heated to 80° C. The desired antibiotic appears as a yellow to greenish spot under these conditions.

The fractions containing the antibiotic were combined and evaporated. The residue was dissolved in 200 ml of chloroform and stirred with an equal volume of 5% sodium phosphate dibasic buffer. The pH was adjusted to 10.0 with 1N NaOH. The phases were separated, and the chloroform was dried over anhydrous sodium sulfate, filtered and evaporated under vacuum.

This material was dissolved in a small amount of acetone and allowed to stand at room temperature, whereupon crystallization occurred. The crystals were collected by filtration and dried under vacuum, yielding 1.5 gm of the product as the sodium salt. A second crop of crystals (1.8 gm) was obtained from the crystal mother liquor.

| | Sodium Salt | | |
|---|---|---|---|
| m.p. | 214–216° C. | | |
| UV | max 275 nm; $E^1$ % 1 cm 0.84 | | |
| Elemental | (Methanol) | | |
| Analysis | C | H | N |
| Found | 62.39 | 8.75 | 0.0 |
| Calc'd. | 63.01 | 9.07 | 0.0 |
| Rotation: $[alpha]_D^{25°}$ = −5.5° (C = 1, CHCl$_3$) | | | |

We claim:
1. A biologically pure culture of the microorganism Streptomyces sp. N664-30, said culture being capable of producing a compound of the formula

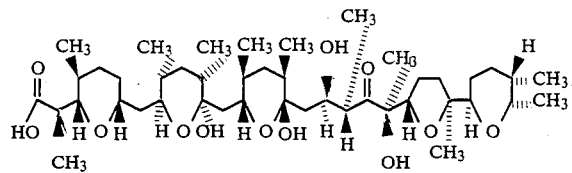

in a recoverable quantity, upon cultivation in an aqueous nutrient medium containing assimilable sources of nitrogen and carbon.

* * * * *